US008409112B2

(12) United States Patent
Wynne et al.

(10) Patent No.: US 8,409,112 B2
(45) Date of Patent: Apr. 2, 2013

(54) SPECIMEN COLLECTION BAG

(75) Inventors: Timothy J. Wynne, Tacoma, WA (US); Jason Birch, Oakland, CA (US)

(73) Assignee: Surgical Principals, Inc., Tacoma, WA (US)

( * ) Notice: Subject to any disclaimer, the term of this patent is extended or adjusted under 35 U.S.C. 154(b) by 291 days.

(21) Appl. No.: 12/731,068

(22) Filed: Mar. 24, 2010

(65) Prior Publication Data

US 2010/0249646 A1    Sep. 30, 2010

Related U.S. Application Data

(60) Provisional application No. 61/163,346, filed on Mar. 25, 2009.

(51) Int. Cl.
*A61B 17/28* (2006.01)
*A61B 10/02* (2006.01)
*A61B 10/06* (2006.01)
*B65D 33/00* (2006.01)

(52) U.S. Cl. ........ 600/562; 606/114; 606/205; 606/206; 606/207; 383/204

(58) Field of Classification Search .................. 600/562; 606/114, 205–207; 383/204
See application file for complete search history.

(56) References Cited

U.S. PATENT DOCUMENTS

| 5,465,731 | A  | * | 11/1995 | Bell et al. ................... 600/562 |
| 5,647,372 | A  | * | 7/1997  | Tovey et al. ................. 600/562 |
| 5,681,324 | A  | * | 10/1997 | Kammerer et al. .......... 606/113 |
| 6,019,770 | A  |   | 2/2000  | Christoudias |
| 6,228,095 | B1 | * | 5/2001  | Dennis ......................... 606/114 |
| 6,346,117 | B1 | * | 2/2002  | Greenhalgh .................. 606/200 |
| 6,350,267 | B1 | * | 2/2002  | Stefanchik ................... 606/114 |
| 6,406,440 | B1 | * | 6/2002  | Stefanchik ................... 600/562 |
| 6,409,733 | B1 |   | 6/2002  | Conlon |
| 7,762,959 | B2 | * | 7/2010  | Bilsbury ....................... 600/564 |
| 2002/0082516 | A1 |   | 6/2002 | Stefanchik |
| 2004/0138587 | A1 |   | 7/2004 | Lyons |
| 2008/0234696 | A1 | * | 9/2008 | Taylor et al. ................. 606/114 |

OTHER PUBLICATIONS

International Search Report and Written Opinion mailed Oct. 27, 2010, in corresponding International Application No. PCT/US2010/028519, filed Mar. 24, 2010, 7 pages.

* cited by examiner

*Primary Examiner* — Sean Dougherty
(74) *Attorney, Agent, or Firm* — Roger M. Rathbun

(57) ABSTRACT

A specimen collection bag includes a flexible bag with a bottom end and a mouth end. A sleeve extends around at least a portion of a perimeter of the mouth end. The sleeve is adapted to receive the jaws of a grasping tool that are movable between a closed position and an open position. Opening the jaws causes the mouth end of the specimen collection bag to open and closing the jaws causes the mouth end of the specimen collection bag to close.

11 Claims, 5 Drawing Sheets

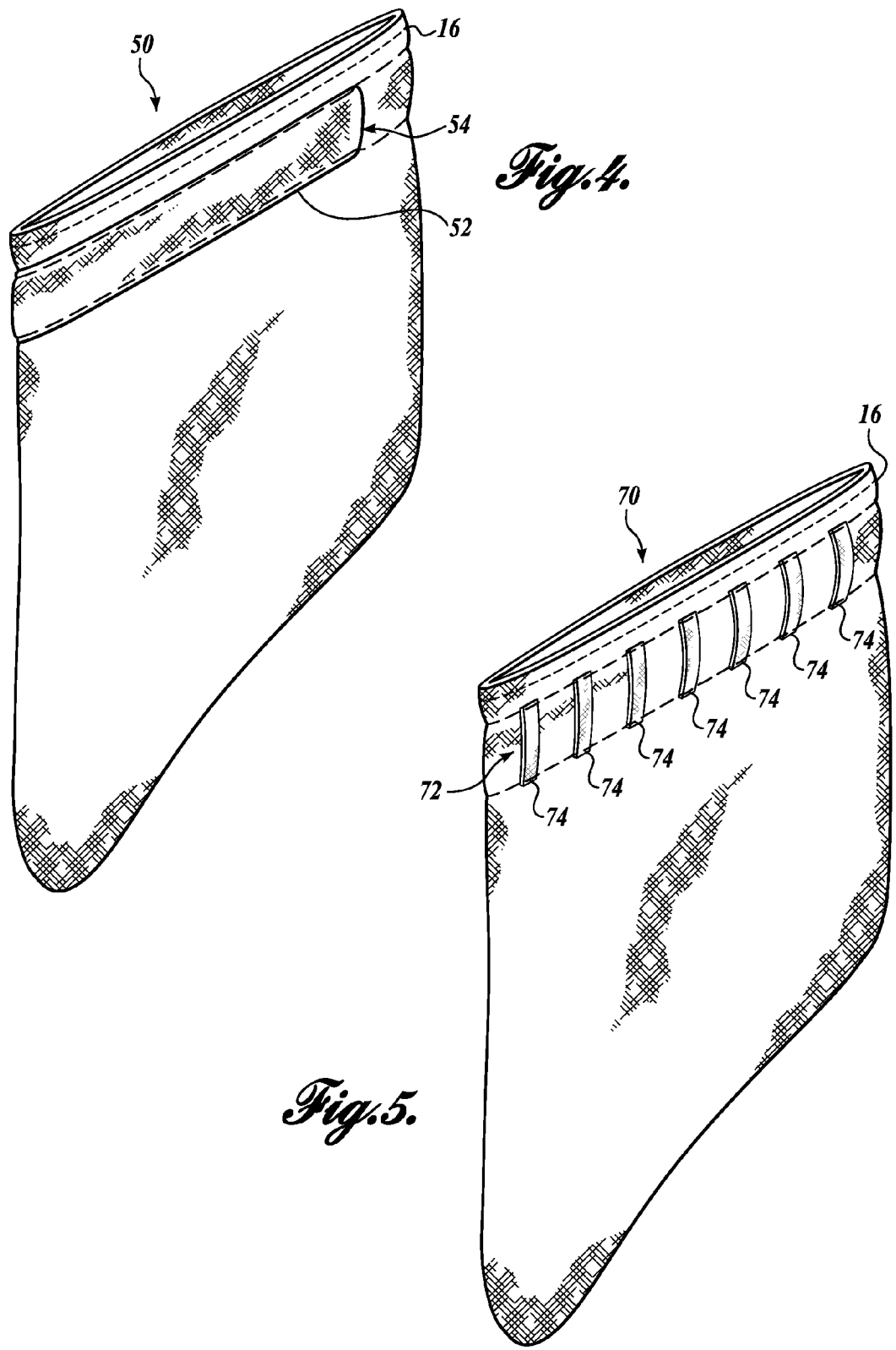

SPECIMEN COLLECTION BAG

CROSS-REFERENCE TO RELATED APPLICATION

The present application claims the benefit under 35 U.S.C. §119(e) of U.S. Provisional Application No. 61/163,346 filed Mar. 25, 2009, which is herein incorporated by reference in its entirety.

BACKGROUND

Specimen collection bags are devices that are used during laparoscopic or other surgical procedures to retrieve tissue, stones or other objects that have been surgically removed from a patient. During use, a specimen retrieval bag is inserted into the patient through an incision, natural orifice or through a trocar. One end of the bag is opened and a surgical tool is used to place the specimen in the bag. The bag is then closed and the removed from the body.

One common problem with conventional specimen collection bags is keeping the bags open in the tight confines of the surgical area. Numerous bag designs have been proposed with spring wires or other self-expanding mechanisms that open one end of the bag upon release. However, such bags often require special tools to deliver and retrieve the bags and are therefore more expensive to manufacture.

Given these problems, there is a need for a specimen collection bag that is easy to open and close, does not require specialized delivery or removal tools and is inexpensive to manufacture.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

To address the problems described above and others, the technology disclosed herein relates to improved specimen collection bags and in particular to laparoscopic specimen collection bags. In one embodiment, a specimen collection bag includes a flexible bag having a closed bottom at a distal end thereof and an open mouth at a proximal end thereof. Surrounding at least a portion of the perimeter of the mouth is a sleeve into which the movable jaws of a grasping tool can be inserted. Opening the jaws while they are in the sleeve opens the mouth of the bag and closing the jaws closes the mouth of the bag.

In one embodiment, the jaws are insertable into the sleeve via a pair of slots in the sleeve. In another embodiment, the sleeve extends only partway around the perimeter of the mouth and the jaws are insertable into the open ends of the sleeve.

In yet another embodiment, the sleeve is formed by a number of loops positioned around at least a portion of the perimeter of the mouth. The jaws of a grasper tool can be inserted into a space between the loops and the inner wall of the bag to open and close the mouth of the bag.

In yet another embodiment of the disclosed technology, the specimen collection bag includes a drawstring in the sleeve.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4 illustrates a specimen collection bag in accordance with another embodiment of the disclosed technology;

FIG. 5 illustrates a specimen collection bag in accordance with yet another embodiment of the disclosed technology;

DETAILED DESCRIPTION

Figure 1:
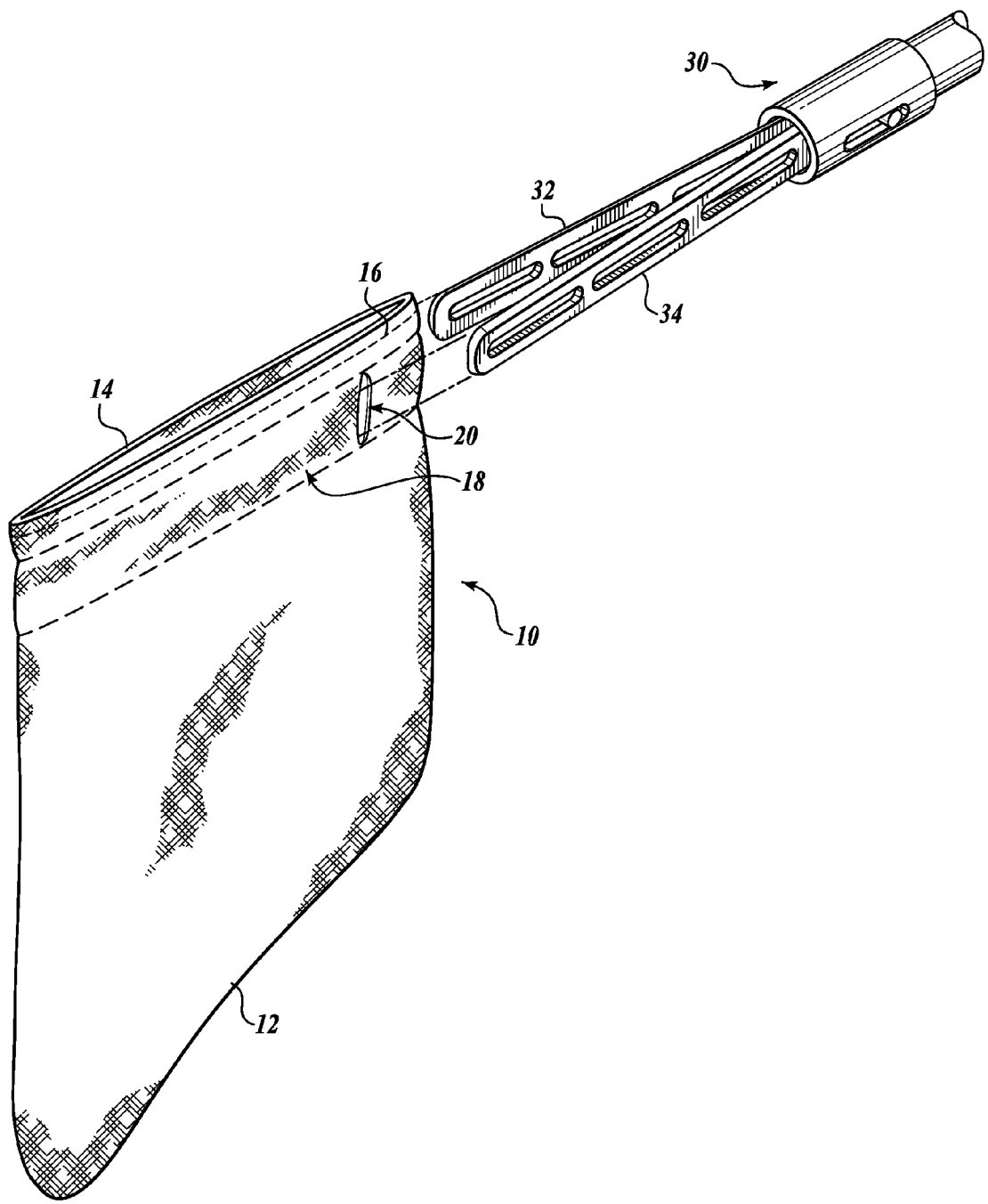
FIG. 1 illustrates a specimen collection bag in accordance with one embodiment of the disclosed technology.

As indicated above, the technology described herein relates to surgical devices and in particular to specimen collection bags. As shown in FIG. 1, a specimen collection bag 10 comprises a flexible bag having a closed bottom 12 at the distal end thereof and an open mouth 14 at the proximal end thereof. In one embodiment, the bag 10 is made of a nylon fabric or other biocompatible material. In some embodiments, the interior of the bag may be lined with a liquid impervious material. In the embodiment shown, the bottom 12 of the bag is tapered so that one end of the bottom is closer to the mouth end than the other end of the bottom. The taper helps the bag to be removed from the patient when the bag contains a specimen. However, the bag 10 may also be configured without a taper. A radio opaque wire 16 is sewn into the bag or is otherwise secured therein to allow the mouth end of the bag to be seen with X-rays. In the embodiment shown, the radio opaque wire 16 is sewn into a fold that extends around the perimeter of the mouth end 14 of the bag.

To allow the specimen collection bag 10 to be opened and closed, the bag 10 includes a sleeve 18 that defines a hollow space between an inner layer and an outer layer of the bag. The sleeve 18 extends around at least a portion of the perimeter of the mouth of the bag. In one embodiment, the sleeve 18 is formed by sewing the inner and outer layers of the bag material together around the perimeter of the mouth. The sleeve 18 also includes a pair of spaced slots 20 (only one visible) to allow access to the hollow space in the sleeve.

A grasping tool 30 is used to open and close the mouth of the bag 10. The grasping tool 30 includes a pair of jaws 32, 34 that are hinged together or are otherwise arranged such that the jaws can be opened and closed by a handle (not shown) at the proximal end of the grasping tool. In one embodiment, the grasping tool 30 is a ratcheted or non-ratcheted laparoscopic bowel grasping tool. Each jaw is inserted into the hollow sleeve 18 through one of the slots 20. The jaws 32, 34 of the grasping tool have a length that is preferably longer than ½ of the diameter of the mouth 14 of the bag and more preferably have a length that is at least ⅔ of the diameter of the mouth 14 of the bag. The width of the sleeve 18 is selected such that the jaws 32, 34 can slide into the sleeve 18 with a relatively snug fit so that the jaws do not easily slide out of the sleeve.

Figure 2:
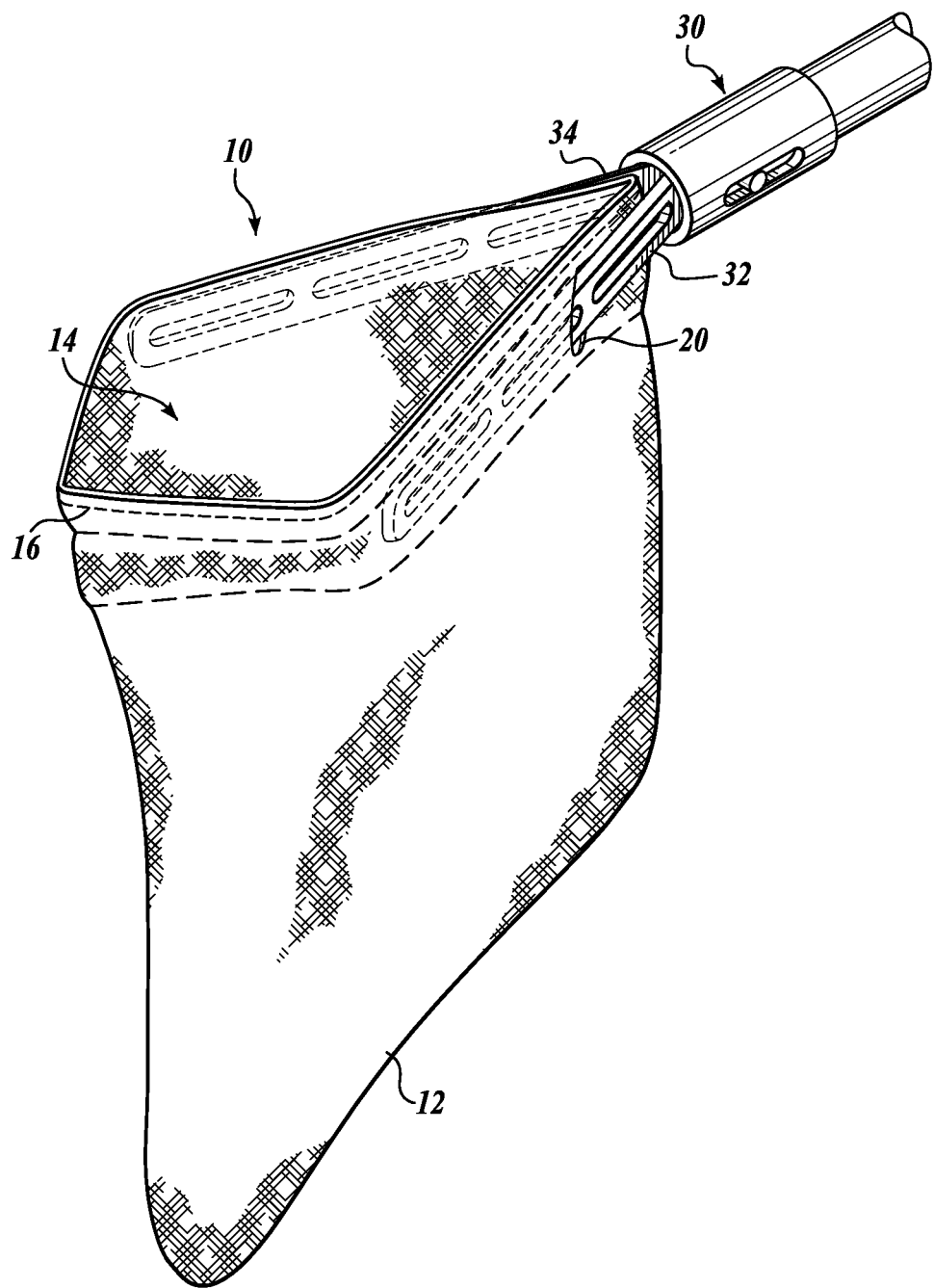
FIG. 2 illustrates a specimen collection bag that is opened with a pair of jaws of a grasping tool in accordance with an embodiment of the disclosed technology.

Activation of the jaws 32, 34 of the grasping tool 30 about the hinge point causes the distal ends of the jaws to spread apart, which in turn causes the mouth 14 of the specimen collection bag 10 to open as shown in FIG. 2. Tissue or other specimen material to be removed from a patient can then be inserted into the open mouth of the bag 10. In one embodiment, the slots 20 in the sleeve 18 are positioned at locations around the perimeter of the mouth 14 such that the distance between the slots 20 on the perimeter is less than the distance between the distal ends of the jaws 32, 34 when in an open position such that the bag 10 cannot be slid off the jaws of the grasping tool 30.

Figure 3:
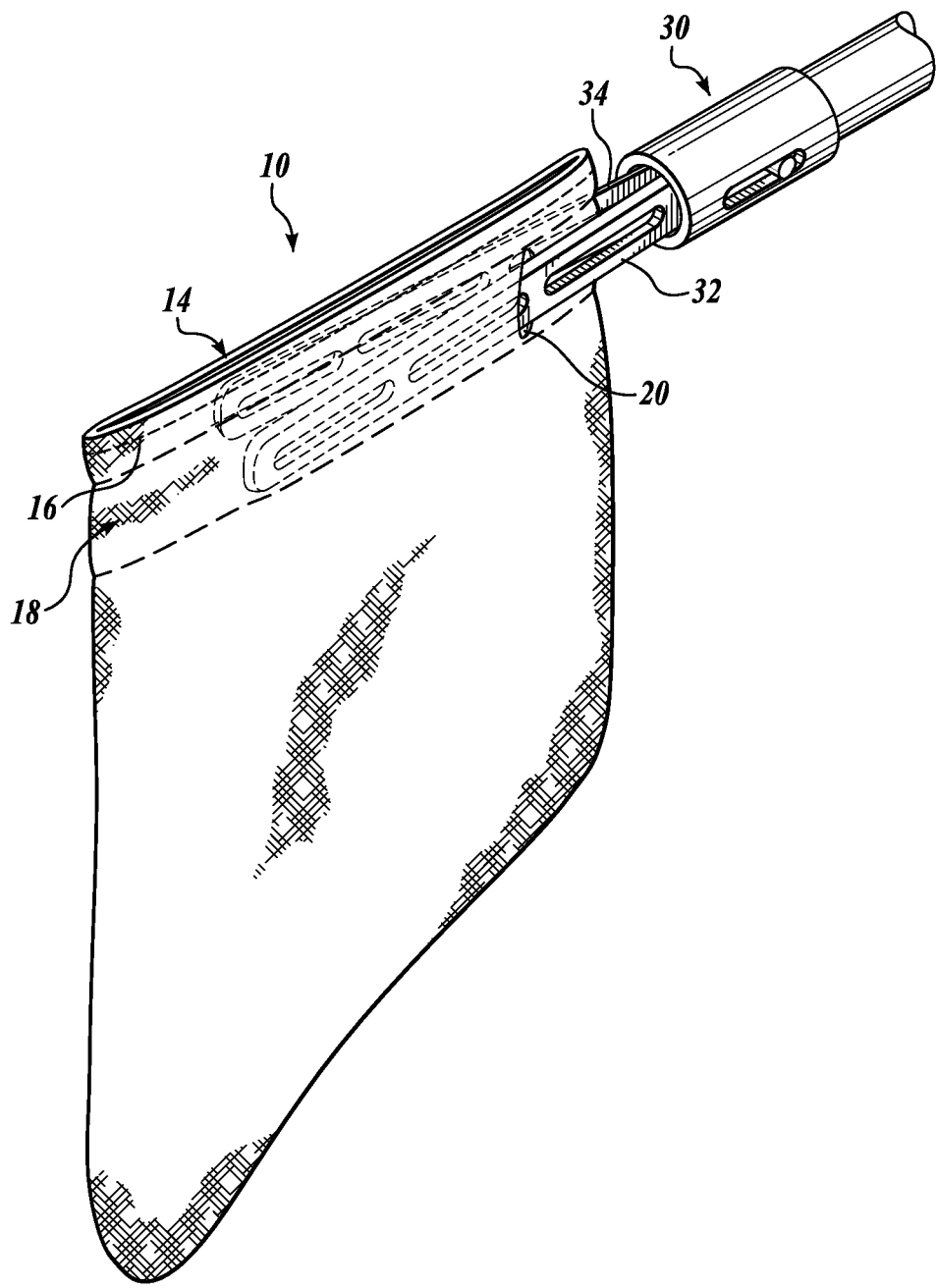
FIG. 3 illustrates a specimen collection bag that is closed with the jaws of a grasping tool in accordance with an embodiment of the disclosed technology.

FIG. 3 illustrates the mouth of the specimen collection bag 10 when the jaws 32, 34 of the grasping tool 30 are in a closed position. If the grasping tool 30 is fully closed, the inward pressure of the jaws 32, 34 against the inner layer of the sleeve 18, closes the mouth 14 of the bag 10. Once closed, the specimen collection bag 10 can be removed from the body by pulling the proximal end of the grasping tool 30 while the jaws are held in the closed position.

Figure 7:
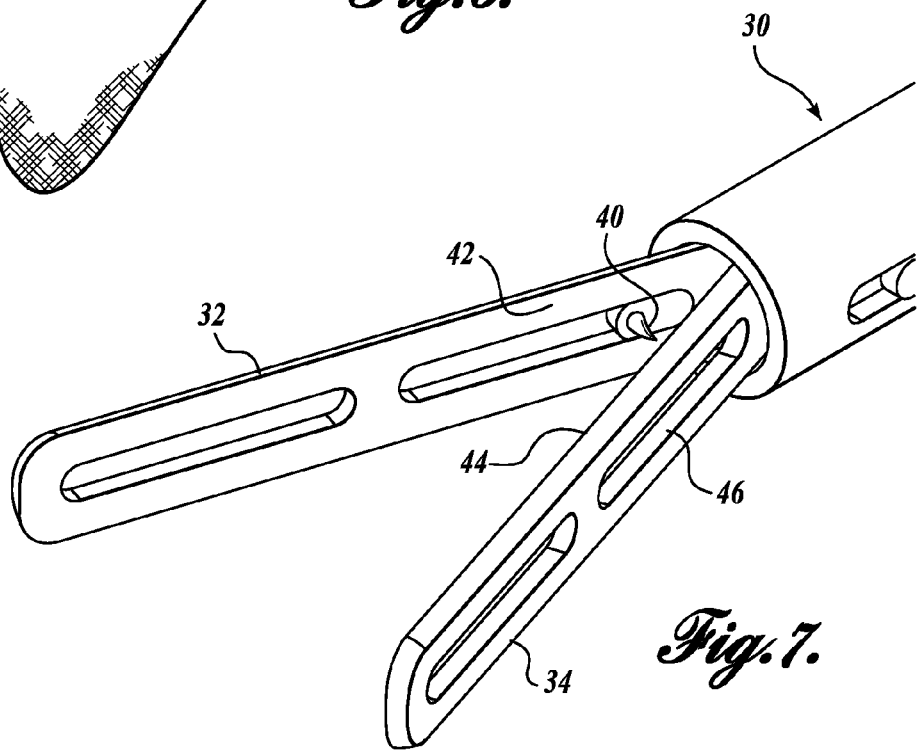
FIG. 7 illustrates a specimen collection bag in accordance with another embodiment of the disclosed technology.

In one embodiment, for example, as can be seen in FIG. 7, the inside face of one of the jaws 32 or 34 includes an inwardly facing pin or "fang" 40 extending from the inside face 42 of one jaw 32 that faces an opposite inside face 44 of the other jaw 34 and curves proximally. Closing the jaws 32 and 34 allows the curved pin 40 to pass through the fabric of the specimen collection bag 10 in order to secure it in place so that the bag does not slide off the grasping tool when the jaws are spaced close together. When the jaws 32 and 34 are in the closed position (see, e.g., FIG. 3), the pin 40 can extend through a hole in the opposite jaw for example, the elongate hole 46 in the second jaw 34 shown in FIGS. 1-3 and 7) to prevent interference of the pin 40 with the full closure of the jaws 32 and 34.

During use in a laparoscopic procedure, the sleeve 18 of the specimen collection bag is threaded onto the jaws 32, 34 of the grasping tool 30. The tool 30 is then held in a closed position while the bag 10 and distal end of the grasping tool 30 are inserted into a patient through a trocar. Once a specimen is ready to be retrieved, the jaws 32, 34 of the grasping tool 30 are opened to open the mouth 14 of the bag. A specimen is then placed in the bag and the jaws 32, 34 of the grasping tool 30 are then closed to close the mouth of the bag. The grasping tool 30 is then removed back through the trocar to retrieve the specimen bag.

FIG. 4 shows an alternative embodiment of a specimen collection bag 50 having a closed bottom and an open mouth. The specimen collection bag has a hollow sleeve 52 that extends only partway around the circumference of the mouth end of the bag. The sleeve 52 is formed by sewing or otherwise forming a hollow space between an inner layer and an outer layer of bag. The ends 54 of the outer layer form the openings into the sleeve 52. The outer layer extends about the perimeter of the mouth such that the distance between the openings into the sleeve 52 is less than the distance between the distal ends of the jaws of the grasping tool when the jaws are opened so that the bag does not slide off the jaws.

FIG. 5 illustrates yet another alternative embodiment of a specimen collection bag 70 according to the disclosed technology. In this embodiment, the bag 70 includes a sleeve 72 that extends around at least a portion of the perimeter of mouth of the bag. The sleeve 72 is formed by a number of loops 74 similar to belt loops on a pair of pants. A grasping tool with jaws is insertable into the hollow space between the inner wall of the bag and the inside of the loops 74 in order to open the mouth of the bag. As will be appreciated, the loops 74 do not need to extend all of the way around the perimeter of the mouth of the bag. In addition, the loops may be spaced at regular or irregular intervals around the perimeter of the mouth of the bag 70.

Figure 6:
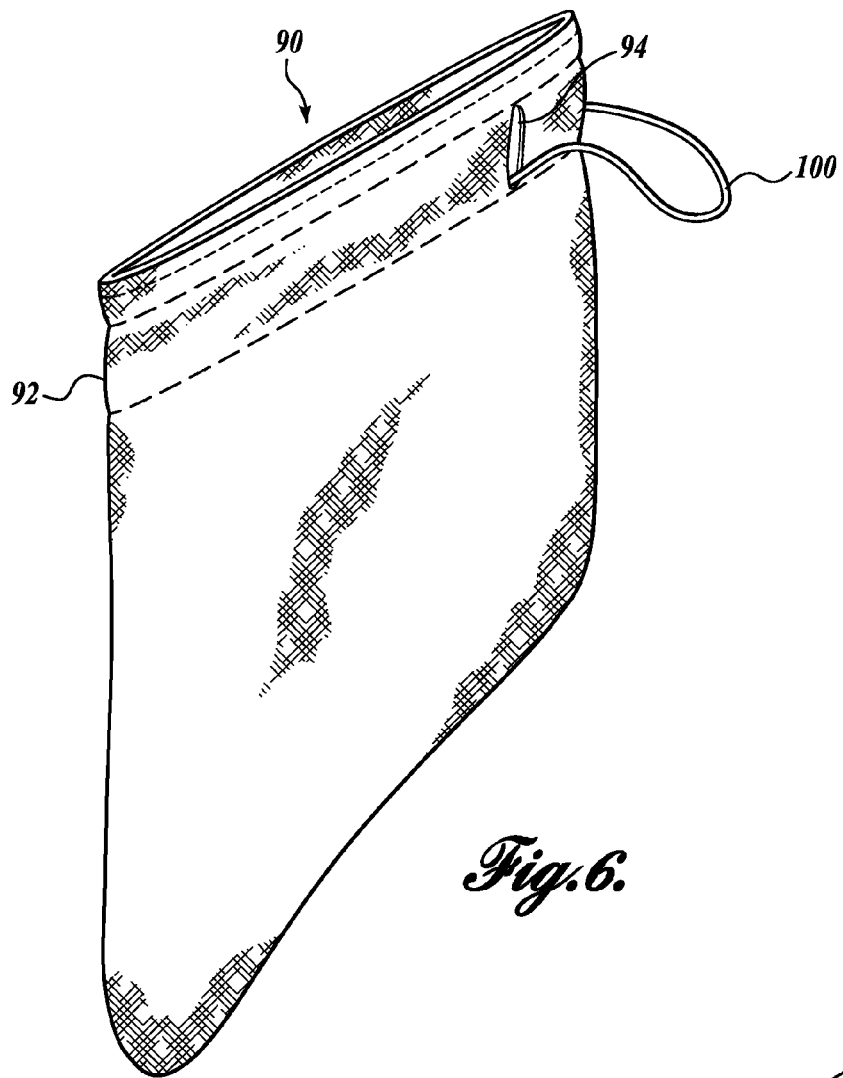
FIG. 6 illustrates a specimen collection bag in accordance with yet another embodiment of the disclosed technology.

FIG. 6 shows yet another embodiment of a specimen collection bag in accordance with the disclosed technology. In this embodiment, a specimen collection bag 90 has a closed bottom end and an open mouth end. The bag 90 also includes a sleeve 92 that defines a hollow space between an inner layer and an outer layer of the bag. The sleeve has a pair of slots 94 into which the jaws of a grasping tool (not shown) can be inserted. The sleeve 92 extends around at least a portion of the perimeter of an open mouth of the bag 90 in the manner described above. The bag 90 also includes a drawstring 100 in the sleeve 92. Pulling the drawstring 100 allows the mouth of the specimen collection bag 90 to be cinched closed when the jaws of a grasping tool are removed from the sleeve 92.

With a conventional specimen collection bag, the surgeon often removes the bag from the body along with the trocar thereby causing a loss of pneumatic pressure in the operating space. The trocar is then reinserted and the operating space re-inflated so that the surgeon can inspect the space and irrigate it, if necessary. One use of the specimen collection bag in accordance with the disclosed technology eliminates the need to re-inflate the operating space. In one embodiment, the drawstring 100 is long enough so that one end can be passed through the trocar cannula to the sterile field outside the patient. The surgeon can place a clamp around the drawstring to cinch the bag closed and suspend it from the distal end of the trocar cannula within the inflated operating space. With the collection bag suspended out of the way, the surgeon can survey the operating space and irrigate it if necessary. Once the surgeon is satisfied that the operating space is clear, the surgeon can then remove the collection bag and trocar cannula from the patient.

While illustrative embodiments have been illustrated and described, it will be appreciated that various changes can be made therein without departing from the scope of the invention. It is therefore intended that the scope of the invention be determined by the following claims and equivalents thereof.

The embodiments of the invention in which an exclusive property or privilege is claimed are defined as follows:

1. A specimen collection system for use with a grasping tool having a pair of movable jaws during a surgical procedure, comprising:
    a flexible bag having a bottom end and a mouth end;
    a grasping tool having a pair of moveable, substantially rigid jaws, at least one of the jaws having an inwardly facing pin on an inner surface; and
    a sleeve extending at least partway around a perimeter of the mouth end of the bag, wherein the sleeve is adapted to receive the jaws of the grasping tool between an inner and an outer layer of the sleeve such that when the jaws are opened in a substantially v-shaped configuration, the mouth end of the bag is opened, and when the jaws are closed in a substantially parallel configuration, the mouth end of the bag is closed and wherein the pin is adapted to grasp the flexible bag when the jaws of the grasping tool are closed together.

2. The specimen collection system of claim 1, wherein the sleeve has openings therein that are adapted to receive the jaws of the grasping tool, wherein the jaws have distal ends, and wherein the openings are spaced apart by a distance that is less than a distance between the distal ends of the jaws when the jaws are in an open position.

3. The specimen collection system of claim 2, wherein the openings are slots in the sleeve.

4. The specimen collection system of claim 1, wherein the bag includes a radio opaque wire around the mouth end of the bag.

5. The specimen collection system of claim 1, wherein the bag is made of a fabric material.

6. The specimen collection system of claim 5, wherein the fabric is nylon.

7. The specimen collection bag system of claim 1, wherein the bag is retained on the jaws of the grasping tool when the grasping tool is in the closed position.

8. A kit for removing a specimen from a surgical site in a patient, comprising:

a grasping tool having a pair of jaws that are movable between a closed position where the distal ends of the jaws are close together in a substantially parallel configuration to an open position where the distal ends of the jaws are spaced apart in a substantially v-shaped configuration, the jaws of the grasping tool further include an inwardly facing pin on an inner surface of one of the jaws of the pair of jaws, wherein the pin is arranged to grasp the specimen collection bag when the jaws of the grasping tool are close together; and a specimen collection bag having a bottom end and a mouth end and a sleeve that extends at least partially around a perimeter of the mouth end, wherein the sleeve is adapted to receive the jaws of the grasping tool such that the mouth end can be opened by moving the jaws of the grasping tool to the open position and closed by moving the jaws of the grasping tool to the closed position.

9. The kit of claim 8, wherein the inwardly facing pin is curved proximally.

10. The kit of claim 8, wherein the sleeve has opening therein that are adapted to receive the jaws of the grasping tool, and wherein the openings are spaced apart by a distance that is less than a distance between distal ends of the jaws when the jaws are in an open position.

11. The kit of claim 10, wherein the openings are slots in the sleeve adapted to receive the jaws of the grasping tool.

\* \* \* \* \*